United States Patent [19]
Hansen et al.

[11] Patent Number: 5,814,496
[45] Date of Patent: Sep. 29, 1998

[54] PROCESS FOR DEMETHYLATING S-METHYL-MERCAPTO COMPOUNDS

[75] Inventors: Theo Adriaan Hansen; Michael Jansen, both of Groningen; Marc Jos E. C. van der Maarel, Haren, all of Netherlands

[73] Assignee: Quest International B.V., Naarden, Netherlands

[21] Appl. No.: 776,129
[22] PCT Filed: Jul. 19, 1995
[86] PCT No.: PCT/EP95/02883
  § 371 Date: Jan. 8, 1997
  § 102(e) Date: Jan. 8, 1997
[87] PCT Pub. No.: WO96/03518
  PCT Pub. Date: Feb. 8, 1996

[30] Foreign Application Priority Data

Jul. 25, 1994 [EP] European Pat. Off. .............. 94202174

[51] Int. Cl.$^6$ ................................ C12P 11/00; C12N 1/20
[52] U.S. Cl. ......................................... 435/130; 435/252.1
[58] Field of Search .................................. 435/130, 252.1

[56] References Cited

PUBLICATIONS

Derwent Biotech Abstract 95–01869 Visscher et al "Demethylation of dimethylsulfonopropionate to 3–mercaptoproprionate by an aerobic marine bacterium" Appl Environ. Microbio. (1994) 60, 12, 4617–4619.

Derwent Biotech Abstract 94–00586 Van der Maarel et al "Anaerobic degradatin of dimethylsulfoniopropionate to 3–S–methylsulfoniopropionate by a marine Desulfobacterium strain" Arch. Microbiol. (1993) 160, 411–12.

Derwent Biotech Abstract 93–14186 Visscher et al "Metabolism of dimethylsulfoniopropionate and nitrate–enhanced consumption of dimethyl sulfide in microbial mats" Abst. Gen Meet Am Soc. Microbiol (1993) 93 Meeting, 353.

*Primary Examiner*—Herbert J. Lilling
*Attorney, Agent, or Firm*—Pillsbury Madison & Sutro LLP

[57] ABSTRACT

The invention concerns a process for preparing mercapto compounds comprising the step of demethylating an S-methyl-mercapto compound of Formula I to the corresponding mercapto compound of Formula II, using a microorganism which is capable of demethylating S-methyl-3-mercapto-propionate (MMPA) to 3-mercaptopropionate (MPA) or using an enzyme preparation derivable from such microorganism.

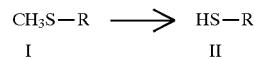

$$CH_3S-R \longrightarrow HS-R$$
$$\text{I} \qquad\qquad \text{II}$$

Preferably the group R denotes $CH_2$—$CH_2$—COOH (I is MMPA), $CH_2$—$CH(NH_2)$—COOH (I is S-methyl-cystein), $CH_2$—$CH_2$—$CH(NH_2)$—COOH (I is methionine) and $CH_2$—COOH (I is methylmercapto-acetate) or a salt or ester of any of these. Preferably the microorganisms are methanogenic archaea of the genus Methanosarcina or obtained by inoculating a suitable medium containing MMPA with salt marsh or marine sediment followed by one or more transfers into fresh medium containing MMPA and suppression of the growth of Bacteria, but not of Archaea in the culture e.g. with an antibiotic.

13 Claims, No Drawings

PROCESS FOR DEMETHYLATING S-METHYL-MERCAPTO COMPOUNDS

This application is the national phase of international application PCT/EP95/02883, filed Jul. 19, 1995.

The invention concerns a process for demethylating S-methyl-mercapto compounds. More particularly the invention concerns a process for microbiologically demethylating S-methyl-mercapto compounds to the corresponding mercapto compounds, such as S-methyl-3-mercaptopropionate to 3-mercaptopropionate.

Various mercapto compounds are useful as flavour components. Thus, 3-mercaptopropionate (hereinafter referred to as MPA for convenience) may be converted into its alkyl esters which, like MPA, are useful as flavour components.

S-methyl-mercaptopropionate (hereinafter referred to as "MMPA" for convenience) is known to be an intermediate in the degradation of 3-dimethylsulphoniumpropionate (also known as dimethyl-β-propiothetin, but hereinafter referred to as DMSP for convenience) in anoxic marine coastal (or intertidal) sediments. A product of this degradation pathway is MPA and it was reported by R. P. Kiene and B. F. Taylor in Appl. Environ. Microbiol. 54: 2208–2212 (1988), and Nature 332: 148–150 (1988), that DMSP may be converted into MMPA which in turn is converted to MPA. MMPA and MPA are also intermediates in the metabolism of DMSP by certain aerobic bacteria, whereas other aerobic bacteria are known to degrade DMSP via an initial cleavage to acrylate and dimethyl sulphide (B. F. Taylor and D. C. Gilchrist, Appl. Environ. Microbiol. 57: 3581–3584 (1991)). Although MMPA is reported to be converted to MPA in coastal sediment (R. P. Kiene, vide supra and P. T. Visscher et al, FEMS Microbiol. Ecol. 14: 179–190 (1994)) the microorganisms responsible for this degradation were unknown and neither was anything known about the efficiency with which this takes place. Furthermore, it was noticed that in such sediments MMPA is also converted into methylmercaptan presumably with concomittant formation of acrylate. Finally, MPA is further metabolized via yet unknown pathways.

It has now been found that certain mercapto compounds can be prepared using a process which comprises the step of demethylating an S-methyl-mercapto compound of general formula I to the corresponding mercapto compound of general formula II, using a microorganism which is capable of demethylating MMPA to MPA, or using an enzyme preparation derivable from such microorganism.

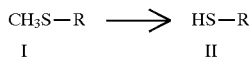

In these general formulae R denotes an alkyl radical derived from an alkane carboxylic acid or a derivative thereof. Examples of such radicals are: $CH_2$—$CH_2$—COOH (I is MMPA), $CH_2$—$CH(NH_2)$—COOH (I is S-methylcystein), $CH_2$—$CH_2$—$CH(NH_2)$—COOH (I is methionine) and $CH_2$—COOH (I is methylmercaptoacetate) and salts or esters of any of these. Such starting materials and various others for the demethylation according to the invention can be prepared from the corresponding dimethylsulphonium compounds by demethylation, whereas these dimethylsulphonium compounds in turn may be found in nature e.g. in various marine organisms and in brassica species and asparagus.

In the process the mercapto compound accumulates in the medium in which the microorganism is cultivated, respectively in the reaction medium in which the enzymatic reaction is carried out, and which contains the S-methylmercapto compound. The reaction product can be isolated therefrom. The process is especially useful for converting MMPA into MPA or derivatives of MMPA into derivatives of MPA.

Suitable microorganisms are methanogenic archaea, especially those occuring in marine and salt marsh sediments, particularly those of the family Methanosarcinaceae, more particularly of the genus Methanosarcina. Examples of such microorganisms are Methanosarcina strain MTP4 (DSM 6636, see also Finster et al, Arch. Microbiol. 157: 425–430 (1992)), *Methanosarcina acetivorans* (particularly DSM 2834) and *Methanosarcina siciliae* (particularly DSM 3028) or similar strains. *Methanosarcina siciliae* was previously known as *Methanolobus siciliae*; see S. Ni, Int. J. Syst. Bact. 44: 357–359 (1994).

Other suitable microorganisms may be found in marine and salt marsh sediments. Therefore the invention also comprises a process in which the demethylation of S-methyl-mercapto compounds of general formula I is performed by a microorganism culture obtained by a process comprising the steps of:

inoculating a suitable medium containing MMPA with salt marsh or marine sediment followed by one or more transfers into fresh medium containing MMPA;

suppressing the growth of Bacteria, but not of Archaea in the culture.

Suitable media are e.g. mineral media containing yeast extract. The minimum concentration of MMPA is preferably 5 mM, more preferably at least 10 mM. A suitable method for suppressing the growth of Bacteria is through minimizing or deleting the presence of nutrients for Bacteria, e.g. minimizing or deleting yeast extract or similar substances from the medium. Alternatively, Bacteria may be removed altogether e.g. by treatment with a suitable antibiotic such as ampicillin, vancomycin or kanamycin.

Without suppression of the growth of Bacteria a substantial part of MMPA (or other S-methyl-mercapto compound) is degraded with formation of methyl mercaptan and thus lost for the demethylation process.

The microorganisms are grown under conditions adapted to the type of microorganism involved. Thus, they are grown under anaerobic conditions in the presence of suitable carbon, nitrogen and other nutrient sources, such as yeast extract. Certain suitable microorganisms may be able to grow using the S-methyl-mercapto compound as the only or main carbon or energy source.

The S-methylmercapto compound (the substrate), e.g. MMPA, is present in the culture medium from the start and/or added to the medium during culturing while care is taken that the substrate concentration does not exceed the level which may retard the growth of the microorganism. Methyl mercaptan may be produced in a side reaction (depending on the microorganism used) and should be removed in a suitable way if their accumulation would retard the growth of the microorganism.

The S-methyl-mercapto compounds used as substrates may in turn be obtained through demethylation of the corresponding dimethylsulphonium compounds, particularly microbiological demethylation using microorganisms or algae which are capable of demethylating DMSP to MMPA, but which are incapable of further demethylating MMPA to MPA with the same or comparable speed, or using an enzyme preparation derivable from such microorganisms. Suitable microorganisms are anaerobic and belong to the group of sulphate reducing microorganisms such as can be found in marine (especially coastal), estuarine and freshwater sediments. Desulfobacterium strains are especially useful, such as *Desulfobacterium autotrophicum, Desulfobacterium vacuolatum* and similar microorganisms. Examples of such microorganisms are Desulfobacterium PM4 (DSM 8278), *Desulfobacterium vacuolatum* (DSM 3385) and *Desulfobacterium autotrophicum* WN (DSM 9180).

Suitable dimethylsulphonium compounds can be found in nature e.g. in various marine organisms and in brassica species and asparagus.

The S-methylmercapto compounds used as substrates in the process of the invention may be prepared in situ in the culture broth by simultaneous demethylation of a dimethylsulphonium compound by a microorganisms or algae which are capable of demethylating DMSP to MMPA, but which are incapable of further demethylating MMPA to MPA with the same or comparable speed. Thus, in a particularly useful embodiment of the invention, a suitable dimethylsulphonium compound is used as the substrate in a process comprising growing a mixed culture of a Desulfobacterium strain, particularly *Desulfobacterium autotrophicum, Desulfobacterium vacuolatum*, more particularly Desulfobacterium PM4 (DSM 8278), *Desulfobacterium vacuolatum* (DSM 3385) and *Desulfobacterium autotrophicum* WN (DSM 9180), on the one hand and a methanogenic microorganism or microorganism culture according to the invention and described above, more particularly Methanosarcina strain MTP4 (DSM 6636), *Methanosarcina acetivorans* and *Methanosarcina siciliae*, on the other hand, under anaerobic conditions. In such mixed culture the dimethylsulphonium compound is first demethylated to the corresponding S-methylmercapto compound which in turn is demethylated to the final mercapto compound. The demethylation of dimethylsulphonium compounds with Desulfobacterium has been described by Van der Maarel et al, Arch. Microbiol. 160: 411–412 (1993) and in copending PCT Application No. 94/01640.

As indicated above, the demethylation of the substrate may also be carried out using an enzyme preparation derivable from the microorganisms capable of performing this reaction. Such enzyme preparation may be obtained directly from these microorganisms, e.g. in the form of homogenized or lysed cells or a further purified product prepared thereof. Also, suitable enzyme preparations may be obtained from other microorganisms to which the genetic information to produce the enzymes necessary for this demethylation has been transferred by genetic engineering. In carrying out such genetic engineering processes the information on the structure of the pertinent enzymes present in the original microorganisms capable of performing the reaction is used.

Without being bound by theory, the enzyme system is thought to be a coenzym M methyl transferase, akin to the specific methyltransferases known to be involved in the metabolism of methanol and methylamines, see J. G. Ferry, Crit. Rev. Biochem. Mol. Biol. 27: 473–503 (1992).

The reaction product of the demethylation reaction according to the invention, including the mercapto compound, e.g. MPA, may be removed from the culture or reaction medium in any suitable way, such as by extraction with a suitable organic solvent, by distillation, by filtration or centrifugation, or by a suitable chromatographic means. If accumulation of the mercapto compound retards the growth of the microorganisms, or if the mercapto compound may be further degraded by the microorganisms, this removal should be done simultaneously with the culturing.

If necessary or desirable the mercapto compound may be further separated or purified from other components possibly present in the reaction product. This purification may be done by methods known in the art.

The mercapto compound may be used as a flavour component as such or after further conversion, e.g. depending on the nature of the group R. Thus, MPA may be converted into an ester, especially a lower alkyl ester in various ways known in the art.

The MPA esters, or other compounds obtained by the demethylation reaction according to the invention, may be used as flavour components in various flavourings and foodstuffs. To this end they may be combined with other flavour components, and if desired with auxiliary substances, solvents, powdered carriers or substrates, in ways known in the art.

In certain cases other sulphur compounds, e.g. dimethylsulphide or methyl mercaptan, may be formed in side reactions during the demethylation process according to the invention and thus be present in the reaction product. From a point of view of use of the reaction product for flavouring purposes, such compounds may sometimes be left in the reaction product because they also may give a useful flavour contribution.

Thus, the product of the process according to the invention may be a reaction product rich in one or more mercapto compounds and possibly other components derived from side reactions, or a further purified mercapto compound, depending on the type of separation step and/or degree of purification used in the process. Alternatively, the process may comprise further steps such as chemically or microbiologically/enzymatically converting the mercapto compound into derivatives thereof.

Flavour components which may be advantageously combined in flavourings and foodstuffs with the mercapto compounds obtained according to the invention are: natural products such as extracts, essential oils, absolutes, resins, concretes, fruit juices, etc., but also synthetic components such as hydrocarbons, alcohols, aldehydes, ketones, esters, ethers, acetals, ketals, acids, etc., including saturated and unsaturated compounds, aliphatic, alicyclic and heterocyclic compounds. Such flavour components are mentioned, for example, in S. Arctander, Perfume and Flavor Chemicals (Montclair, N.J., 1969), in S. Arctander, Perfume and Flavor Materials of Natural Origin (Elizabeth, N.J., 1960), in T. E. Furia et al., CRC Fenaroli's Handbook of Flavor Ingredients, 2nd edition (Cleveland, CRC Press Inc., 1975), H. B. Heath, Source Book of Flavours, The Avi Publishing Co. Inc. Westport, Conn. (1981) and in "Flavor and Fragrance Materials—1989", Allured Publishing Co. Wheaton, Ill. USA. Auxiliary substances and solvents which can be used in flavour compositions containing the mercapto compounds obtained according to the invention are, for example: ethanol, isopropanol, diethyleneglycol monoethyl ether, glycerol, triacetin etc. Powdered substrates or carriers may include salt, starch derivatives and the like. Processing into a powdered product may include spray-drying and other techniques of micro-encapsulation.

EXAMPLE 1

Methanosarcina sp. strain MTP4 (DSM 6636, obtainable from the Deutsche Sammlung von Mikroorganismen und Zellkulturen in Braunschweig, Germany) was grown at 30° C. in 120 ml bottles filled with 50 ml medium according to Finster et al, Arch. Microbiol. 157: 425–430 (1992) under an atmosphere of $N_2/CO_2$ (80:20) and inoculated with a late-log phase culture. Growth was followed by measuring the optical density at 430 nm. When a methanol-grown culture was transferred to a medium containing MMPA as the substrate a lag phase of about 7 days was observed. A culture previously grown on MMPA showed no such lag phase. 13.5 mM MMPA was converted into 13.5 mM MPA, while 10.2 mM methane was detected. MPA could be obtained from the culture broth by HPLC after centrifugation to remove cells, as described by Van der Maarel et al Arch. Microbiol. 160: 411–412 (1993). Without lag phase the conversion was complete in about 150 hours.

EXAMPLE 2

Example 1 was repeated using *Methanosarcina acetivorans* (DSM 2834 obtainable from the Deutsche Sammlung von Mikroorganismen und Zellkulturen in Braunschweig, Germany) in a medium as described in the DSM catalogue of strains 1993, at 37° C. In this case a concentration of 5 g/l MMPA was nearly quantitatively converted into MPA.

EXAMPLE 3

A sample of anoxic marine intertidal sediment was collected from the Waddensea near Westernieland, the Netherlands and transported in a $N_2$-flushed anaerobic jar at ambient temperature. Suspensions were made in degassed seawater (4 ml per gram wet weight of sediment) in an anaerobic glove box within a few hours from collection of the sample. The suspensions were thoroughly mixed for one minute with a blender and 40 ml aliquots were poured into 70 ml bottles while the sediment was kept in suspension. The bottles were sealed with screw caps containing a butyl rubber stopper through the central hole and a viton disc beneath the rubber stopper. The headspace was flushed with oxygen-free nitrogen for 2 minutes, ampicillin, vancomycin or kanamycin was added to a concentration of 20 $\mu$g/ml and the suspension was incubated overnight at 20° C.

In a 120 ml bottle 50 ml of bicarbonate (50 mM) buffered mineral medium according to Heijthuijsen et al, Appl. Environ. Microbiol. 55: 965–969 (1989), containing 20 mM sulphate, 50 mg/l yeast extract and 20 mM MMPA was incubated with 2.5 ml of a sediment suspension obtained above and cultured at 28° C. After several transfers into fresh medium the sulphate was omitted from the medium. The MMPA added to the medium was quantitatively converted into MPA and methane.

Epifluorescence microscopy of the culture showed large numbers of irregular coccoid cells having a characteristic fluorescence at 420 nm; the cells were morphologically similar to Methanosarcina.

We claim:

1. Process for preparing a mercapto compound which comprises demethylating an S-methylmercapto compound according to general formula I, wherein R denotes an alkyl radical derived from an alkanecarboxylic acid or derivative thereof, to the corresponding mercapto compound of general formula II,

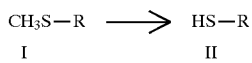

$$CH_3-R \longrightarrow HS-R$$
$$\quad I \qquad\qquad II$$

using a preparation selected from the group consisting of microorganism cultures and enzyme preparations derivable from such microorganism cultures, said microorganism culture being obtained by:
(a) inoculating a suitable medium containing S-methyl-3-mercaptopropionate (MMPA) with salt marsh or marine sediment followed by one or more transfers into fresh medium containing MMPA;
(b) suppressing the growth of Bacteria, but not of Archaea in the culture.

2. Process for preparing a mercapto compound which comprises demethylating an S-methyl-mercapto compound according to general formula I, wherein R denotes an alkyl radical derived from an alkanecarboxylic acid or derivative thereof, to the corresponding mercapto compound of general formula II,

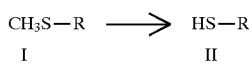

$$CH_3-R \longrightarrow HS-R$$
$$\quad I \qquad\qquad II$$

using a microorganisms which is selected from the group consisting of methanogenic archaeons and enzyme preparations derivable from such microorganism.

3. Process according to claim 1 or 2 wherein in the S-methylmercapto compound R denotes a group selected from the group consisting of $CH_2-CH_2-COOH$ (I is MMPA), $CH_2-CH(NH_2)-COOH$ (I is S-methyl-cystein), $CH_2-CH_2-CH(NH_2)-COOH$ (I is methionine) and $CH_2-COOH$ (I is methylmercapto-acetate) and salts or esters of any of these.

4. Process according to claim 3 wherein the S-methylmercapto compound is MMPA and the resulting mercapto compound is MPA.

5. Process according to claim 2 wherein the methanogenic archaeon belongs to the genus Methanosarcina.

6. Process according to claim 5 wherein the Methanosarcina strain is Methanosarcina strain MPT4, *Methanosarcina acetivorans* or *Methanosarcina siciliae* or similar strain.

7. Process according to claim 5 wherein the Methanosarcina strain is Methanosarcina strain MPT4 DSM 6636, *Methanosarcina acetivorans,* or *Methanosarcina siciliae.*

8. Process according to claim 1 wherein the growth of Bacteria is suppressed by the addition of an antibiotic.

9. Process according to claim 1 wherein the S-methylmercapto compound is prepared in situ in the culture broth by simultaneous demethylation of a corresponding dimethylsulphonium compound by a microorganism or algae which is capable of demethylating 3-dimethylsulphoniumpropionate to S-methyl-3-mercaptopropionate, which microorganism or algae is grown in mixed culture with the microorganism which is capable of demethylating S-methyl-3-mercaptopropionate (MMPA) to 3-mercaptopropionate (MPA).

10. Process according to claim 9 wherein the microorganism which is capable of demethylating 3-dimethylsulphoniumpropionate to S-methyl-3-mercaptopropionate is a Desulfobacterium strain.

11. Process according to claim 10 wherein the Desulfobacterium strain is Desulfobacterium PM4 DSM 8278, *Desulfobacterium vacuolatum* DSM 3385 or *Desulfobacterium autotrophicum* WN DSM 9180.

12. Process according to claim 1 wherein the enzyme is a coenzyme M methyl transferase.

13. A process for preparing a mercapto compound which comprises demethylating an S-methyl-mercapto compound of the formula I:

$$CH_3-R$$

where R stands for an alkyl radical to form the corresponding mercapto compound of the formula:

$$HS-R$$

using the microorganism culture of claim 1 which is capable of demethylating S-methyl-3-mercapto-propionate to 3-mercaptopropionate.

* * * * *